US010775322B2

(12) United States Patent
Conrad et al.

(10) Patent No.: US 10,775,322 B2
(45) Date of Patent: Sep. 15, 2020

(54) INERT CRYSTAL DELIVERY MEDIUM FOR SERIAL FEMTOSECOND CRYSTALLOGRAPHY

(71) Applicant: ARIZONA BOARD OF REGENTS ON BEHALF OF ARIZONA STATE UNIVERSITY, Scottsdale, AZ (US)

(72) Inventors: Chelsie Conrad, Phoenix, AZ (US); Petra Fromme, Mesa, AZ (US); Daniel James, Mesa, AZ (US); Christopher Kupitz, Scottsdale, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 349 days.

(21) Appl. No.: 15/183,149

(22) Filed: Jun. 15, 2016

(65) Prior Publication Data

US 2016/0370306 A1    Dec. 22, 2016

Related U.S. Application Data

(60) Provisional application No. 62/180,326, filed on Jun. 16, 2015.

(51) Int. Cl.
| | | |
|---|---|---|
| *G01N 23/20* | (2018.01) | |
| *G01N 23/207* | (2018.01) | |
| *C30B 29/58* | (2006.01) | |
| *G01N 33/483* | (2006.01) | |
| *C30B 7/14* | (2006.01) | |
| *G01N 23/2005* | (2018.01) | |

(52) U.S. Cl.
CPC .......... *G01N 23/2005* (2013.01); *C30B 7/14* (2013.01); *C30B 29/58* (2013.01); *G01N 33/483* (2013.01)

(58) Field of Classification Search
CPC .... G01N 23/2005; G01N 33/483; C30B 7/14; C30B 29/58; A01N 1/0221
USPC .............................. 506/7; 436/18; 422/245.1
See application file for complete search history.

(56) References Cited

U.S. PATENT DOCUMENTS

| | | | | |
|---|---|---|---|---|
| 5,071,741 | A * | 12/1991 | Brockbank | A01N 1/02 128/898 |
| 2005/0205005 | A1* | 9/2005 | Hansen | C30B 7/14 117/206 |
| 2006/0137603 | A1* | 6/2006 | Bukshpan | C07K 1/306 117/68 |
| 2009/0018029 | A1 | 1/2009 | Miao et al. | |
| 2013/0299099 | A1* | 11/2013 | Mori | C30B 5/00 159/16.1 |
| 2016/0051995 | A1 | 2/2016 | Weierstall et al. | |

OTHER PUBLICATIONS

Biertumpfel, C. (2002). "Crystallization of biological macromolecules using agarose gel." Acta Crystallogr D Biol Crystallogr. 58: 1657-9. (Year: 2002).*

(Continued)

*Primary Examiner* — Benjamin R Whatley
*Assistant Examiner* — Jacqueline Brazin
(74) *Attorney, Agent, or Firm* — Quarles & Brady LLP; Jessica L. Lewis

(57) ABSTRACT

A system and method for preparing a crystal delivery medium comprising agarose for serial femtosecond crystallography and uses thereof.

14 Claims, 10 Drawing Sheets
(10 of 10 Drawing Sheet(s) Filed in Color)

(56) References Cited

OTHER PUBLICATIONS

Pflugrath, JW. (2015). "Practical macromolecular cryocrystallography." Acta Crystallogr F Struct Biol Commun. 71(622-42). (Year: 2015).*
Wang, L. et al. (2008). "Kinetic Analysis of Protein Crystal Nucleation in Gel Matrix." Biophys J. 95(12). 5931-5940. (Year: 2008).*
Pemberton, TA et al. (2012). "Proline: Mother Nature's cryoprotectant applied to protein crystallography." Acta Crys. D68. 1010-1018. (Year: 2012).*
Kozuka, M. (2015). "Rapid and Simple Purification of Lysozyme from the Egg SHell Membrane." J Nutr Sci Vltaminol. 61(101-103). (Year: 2015).*
Hampton Research. Solutions for Crystal Growth. https://hamptonresearch.com/categories.php Webpage accessed Jun. 9, 2020 (Year: 2020).*
Aquila, A. et al. (2012). Time-resolved protein nanocrystallography using an X-ray free-electron laser. Opt. Express, 20, 3, 2706-2716.
Arnott, S., et al. (1974). The agarose double helix and its function in agarose gel structure. J. Mol. Biol. 90, 269-284.
Axford, D. et al. In cellulo structure determination of novel cypovirus polyhedrin. Acta Cryst. D70, 1435-1441 (2014).
Aishima, J., et al. High-speed crystal detection and characterization using a fast-readout detector. Acta Crystallographica Section D-Biological Crystallography 66, 1032-1035 (2010).
Barty, A., et al. (2012). Self-terminating diffraction gates femtosecond X-ray nanocrystallography measurements. Nat. Photonics, 6, 35-40.
Barty, A., et al. (2014). Cheetah:software for high-throughput reduction and analysis of serial femtosecong X-ray diffraction data. J. Appl. Cryst. 47, 1118-1131.
Biertumpfel, C., et al. (2002). Crystallization of biological macromolecules using agarose gel. Acta Cryst. D58, 1657-1659.
Botha, S. et al. (2015). Room-temperature serial crystallography at synchroton X-ray sources using slowly flowing free-standing high-viscosity microstreams. Acta Cryst. D71, 387-397.
Boutet, S. et al. (2012). High-resolution protein structure determination by serial femtosecond crystallography. Science, 337, 362-364.
Boutet, S. & Williams, G. J. (2010). The coherent X-ray imaging (CXI) instrument at the Linac Coherent Light Source (LCLS). New J. Phys. 12, 035024.
Brehm, W. & Diederichs, K. (2014). Breaking the indexing ambiguity in serial crystallography. Acta Cryst. D70, 101-109.
Caffrey, M. (2015). A comprehensive review of the lipid cubic phase or in meso method for crystallizing membrane and soluble proteins and complexes. Acta Cryst. F71, 3-18.
Caffrey, M. & Cherezov, V. (2009). Crystallizing membrane proteins using lipidic mesophases. Nat. Protoc. 4, 706-731.
Chapman, H. N. et al. (2011). Femtosecond X-ray protein nanocrystallography. Nature, 470, 73-77.
Cheng, A., Hummel, B., Qiu, H. & Caffrey, M. (1998). A simple mechanical mixer for small viscous lipid-containing samples. Chem. Phys. Lipids, 95, 11-21.
Cherezov, V. (2011). Lipidic cubic phase technologies for membrane protein structural studies. Curr. Opin. Struct. Biol. 21, 559-566.
Deponte, D. P., Weierstall, U., Schmidt, K., Warner, J., Starodub, D., Spence, J. C. H. & Doak, R. B. (2008). Gas dynamic virtual nozzle for generation of microscopic droplet streams. J. Phys. D Appl. Phys. 41, 195505.
Fenalti, G. et al. (2015). Structural basis for bifunctional peptide recognition at human δ-opiod receptor. Nat. Struct. Mol. Biol. 22, 265-268.
Fromme, P. & Witt, H. T. (1998). Improved isolation and crystallization of Photosystem I for structural analysis. Biochim. Biophys. Acta, 1365, 175-184.
Garcia-Ruiz, J. M., Novella, M. L., Moreno, R. & Gavira, J. A. (2001). Agarose as crystallization media for proteins I: Transport processes. J. Cryst. Growth, 232, 165-172.

Hopkins, A. L. & Groom, C. R. (2002). The druggable genome. Nat. Rev. Drug Discov. 1, 727-730.
Hunter, M. S. & Fromme, P. (2011). Toward structure determination using membrane-protein nanocrystals and microcrystals. Methods, 55, 387-404.
Johansson, L. C. et al. (2013). Structure of a photosynthetic reaction centre determined by serial femtosecond crystallography. Nat. Commun. 4, 2911.
Johansson, L. C. et al. (2012). Lipidic phase membrane protein serial femtosecond crystallography. Nat. Methods, 9, 263-265.
Jordan, P., Fromme, P., Witt, H. T., Klukas, O., Saenger, W. & Krauis, N. (2001). Three-dimensional structure of cyanobacterial photosystem I at 2.5Å resolution. Nature, 411, 909-917.
Karplus, P. A. & Diederichs, K. (2012).Linking crystallographic model and data quality. Science, 336, 1030-1033.
Kirian, R. A., Wang, X., Weierstall, U., Schmidt, K. E., Spence, J. C., Hunter, M., Fromme, P., White, T., Chapman, H. N. & Holton, J. (2010). Femtosecond protein nanocrystallography—data analysis methods. Opt. Express, 18, 5713-5723.
Kirian, R. A., White, T. A., Holton, J. M., Chapman, H. N., Fromme, P., Barty, A., Lomb, L., Aquila, A., Maia, F. R. N. C., Martin, A. V., Fromme, R., Wang, X., Hunter, M. S., Schmidt, K. E. & Spence, J. C. H. (2011). Structure-factor analysis of femtosecond microdiffraction patterns from protein nanocrystals. Acta Cryst. A67, 131-140.
Kissick, D. J.,Wanapun, D. & Simpson, G. J. (2011). Second-order nonlinear optical imaging of crystals. Annu. Rev. Anal. Chem. 4, 419-437.
Kupitz, C. et al. (2014). Serial time-resolved crystallography of photosystem II using a femtosecond X-ray laser. Nature, 513, 261-265.
Koopmann, R. et al. In vivo protein crystallization opens new routes in structural biology. Nature Methods 9, 259-262 (2012).
Landau, E. M. & Rosenbusch, J. P. (1996). Lipidic cubic phases: a novel concept for the crystallization of membrane proteins. Proc. Natl Acad. Sci. USA, 93, 14532-14535.
Lawrence, R.M., Conrad, C. E., Grant, T. D., Zatsepin, N. A., Liu, H., James, D., Nelson, G., Subramanian, G., Aquila, A., Hunter, M. S., Liang, M., Boutet, S., Coe, J., Spence, J. C. H.,Weierstal, U., Liu,W., Fromme, P., Cherezov, V., Snell, E. & Hogue, B. G. (2015). Serial femtosecond X-ray diffraction of enveloped virus microcrystals. Structural Dynamics 2, 041720.
Liu, W. et al. (2013). Serial femtosecond crystallography of G-protein coupled receptors. Science, 342, 1521-1524.
Lorber, B., Sauter, C., The'obald-Dietrich, A., Moreno, A., Schellenberger, P., Robert, M.-C., Capelle, B., Sanglier, S., Potier, N. & Giege', R. (2009). Crystal growth of proteins, nucleic acids, and viruses in gels. Prog. Biophys. Mol. Biol. 101, 13-25.
McCoy, A. J. (2007). Solving structures of protein complexes by molecular replacement with Phaser. Acta Cryst. D63, 32-41.
Neutze, R., Huldt, G., Hajdu, J. & van der Spoel, D. (2004). Potential impact of an X-ray free electron laser on structural biology. Radiat.Phys. Chem. 71, 905-916.
Redecke, L. et al. Natively Inhibited Trypanosoma brucei Cathepsin B Structure Determined by Using an X-ray Laser. Science 339, 227-230 (2013).
Saridakis, E. & Chayen, N. E. (2003). Systematic improvement of protein crystals by determining the supersolubility curves of phase diagrams. Biophys. J. 84, 1218-1222.
Schirmer, T., Bode, W., Huber, R., Sidler, W. & Zuber, H. (1985). X-ray crystallographic structure of the light-harvesting biliprotein C-phycocyanin from the thermophilic cyanobacterium Mastigocladus laminosus and its resemblance to globin structures. J. Mol. Biol. 184, 257-277.
Sierra, R. G. et al. (2012). Nanoflow electrospinning serial femtosecond crystallography. Acta Cryst. D68, 1584-1587.
Sugahara, M. et al. (2015). Grease matrix as a versatile carrier of proteins for serial crystallography. Nat. Methods, 12, 61-63.
Schonherr, R. et al. Real-time investigation of dynamic protein crystallization in living cells. Structural dynamics 2, 041712(1-17) (2015).

(56) References Cited

OTHER PUBLICATIONS

Sawaya, M,R. et al. Protein crystal structure obtained at 2.9 Å resolution from injecting bacterial cells into an X-ray free electron laser beam. PNAS 111, 12769-12774 (2014).

Weierstall, U. et al. (2014). Lipidic cubic phase injector facilitates membrane protein serial femtosecond crystallography. Nat. Commun. 5, 3309.

White, T. A., Kirian, R. A., Martin, A. V., Aquila, A., Nass, K., Barty, A. & Chapman, H. N. (2012). CrystFEL: a software suite for snapshot serial crystallography. J. Appl. Cryst. 45, 335-341.

Zhang, H. et al. (2015). Structure of the angiotensin receptor revealed by serial femtosecondcrystallography. Cell, 161(4), 833-844.

Phillips, "The three-dimensional structure of an enzyme molecule," Scientific American, Nov. 1966, p. 78-90.

Caffrey, "Membrane protein crystallization," Journal of Structural Biology, 142, 2003, p. 108-132.

* cited by examiner (A)

(B)

(C)

(D)

(A)

(B)

(C)

(A)

(B)

(C)

(D)

(A)

(D)

(B)

(E)

(C)

(F)

(A)

(B)

(A)          (B)

INERT CRYSTAL DELIVERY MEDIUM FOR SERIAL FEMTOSECOND CRYSTALLOGRAPHY

CROSS-REFERENCE TO RELATED APPLICATIONS

This application claims priority to U.S. Provisional Patent Application No. 62/180,326, filed Jun. 16, 2015, which is incorporated herein by reference as if set forth in its entirety.

STATEMENT REGARDING FEDERALLY SPONSORED RESEARCH

This invention was made with government support under R21 GM095583 awarded by the National Institutes of Health and 1231306 awarded by the National Science Foundation. The government has certain rights in the invention.

BACKGROUND

Serial femtosecond crystallography (SFX) is a novel structural biology technique that allows challenging protein structures to be solved from sub-micrometer/micrometer sized crystals at room temperature (Chapman et al., 2011). In SFX, nanocrystals and/or microcrystals are delivered in a liquid (DePonte et al., 2008) or a viscous stream (Weierstall et al., 2014) into the beam path of a hard X-ray free-electron laser (XFEL). XFEL radiation is composed of femtosecond pulses typically delivered at a rate of 1-120 Hz, and diffraction patterns are obtained before the crystals are destroyed (Neutze et al., 2004; Barty et al., 2012). SFX currently requires large data sets because the diffraction patterns are acquired from individual randomly oriented protein crystals. Most SFX experiments thus far have been based on protein crystals delivered using a gas dynamic virtual nozzle (GDVN), where the crystals are delivered to the X-ray beam in their mother liquor (DePonte et al., 2008).

The gas-focused GDVN liquid jet moves at a velocity of 10-20 m s$^{-1}$, which delivers crystals much faster than required to replenish the protein crystals between X-ray pulses at a pulse repetition rate of 120 Hz. Therefore, approximately only one out of every 10,000 crystals is probed by the X-ray pulses (Weierstall et al., 2014). This type of liquid jet can consume 10-100 mg of protein for the collection of a complete data set, which is particularly problematic for membrane proteins and other proteins that can only be produced in small amounts.

Membrane proteins are an important class of proteins that are of very high relevance in biology, compromising 60% of all current drug targets (Hopkins & Groom, 2002). However, structure determination of membrane proteins lags far behind soluble protein structure determination, with less than 550 unique membrane-protein structures determined so far out of over 100,000 structures currently deposited in the Protein Date Bank.

Membrane proteins are insoluble in water and therefore have to be extracted from the membrane in the form of protein-detergent micelles. Most membrane-protein structures are obtained by either crystallization in solution in the form of protein-detergent micelles or crystallization in the lipidic environment of the lipidic cubic phase (LCP), a method for membrane-protein crystallization pioneered by Landau & Rosenbusch (1996).

LCP is a liquid crystalline phase that is spontaneously formed upon mixing monoacylglycerols (MAGs) and water, producing a continuous three-dimensional network of curved bilayers arranged into a cubic lattice with two networks of interconnecting continuous aqueous channels (Caffrey, 2015). The architecture of the lipid formation encourages type 1 crystal packing and has similar properties to the native cell membrane (Caffrey, 2015). Crystallization in LCP has been successful for structure determination of a wide range of membrane proteins, including microbial rhodopsins, photosynthetic complexes, β-barrels, enzymes, transporters, ion channels and especially G-protein-coupled receptors (GPCRs), a class of membrane proteins with high medicinal impact (Cherezov, 2011).

A new crystal-delivery system has been developed for SFX which allows the delivery of crystals grown in LCP to the XFEL beam (Weierstall et al., 2014). The high viscosity of LCP results in a much slower flow rate of the stream, thus drastically decreasing the net mass of protein needed for structure determination by SFX. LCP as a delivery medium has been successfully used to determine GPCR structures using an XFEL (Liu et al., 2013; Fenalti et al., 2015; Weierstall et al., 2014; Zhang et al., 2015). Crystallization of membrane proteins in LCP has been highly optimized, contributing to the structures of over 60 unique membrane proteins to date (Caffrey & Cherezov, 2009). However, it has been challenging to crystallize large multi-domain membrane complexes in LCP owing to the curvature associated with the lipid bilayer and the low diffusion constants of large membrane-protein complexes in LCP. To date, the majority of membrane-protein structures solved by X-ray crystallography have been determined from crystals of protein-detergent micelles grown in solution, which have also been successfully used for SFX experiments (Chapman et al., 2011; Aquila et al., 2012; Johansson et al., 2012, 2013; Kupitz et al., 2014). These membrane-protein crystals were delivered either with the GDVN liquid injector (DePonte et al., 2008), requiring large amounts of protein, the gel injector (lipidic cubic phase injector; Weierstall et al., 2014) or an electrospinning injector (Sierra et al., 2012), which uses less protein but uses high electric fields which could be problematic for crystal stability.

To date, all membrane-protein structures delivered in LCP for SFX (Weierstall et al., 2014; Liu et al., 2013; Fenalti et al., 2015; Zhang et al., 2015) have been based on crystals that were grown in LCP. Mixing of membrane-protein crystals grown in the form of a protein-detergent micelle with LCP typically leads to dissolution of the crystals, very likely caused by partitioning of the detergent, which forms the protein-detergent micelle, into the lipidic phase. This leads to depletion of the detergent in the protein-detergent micelles in the crystals, resulting in denaturation of the protein. Recently, two other viscous media, a mineral oil-based grease and petroleum jelly, have been described as alternative crystal-delivery carriers (Sugahara et al., 2015; Botha et al., 2015). The grease mixture (Sugahara et al., 2015) has been used to deliver crystals to the XFEL beam for SFX data collection of soluble model proteins at the SPring-8 Compact Free Electron Laser (SACLA XFEL), while petroleum jelly (Botha et al., 2015) has been used to deliver lysozyme at the Swiss Light Source (SLS). Both of these delivery methods have so far only been demonstrated at ambient pressure and they produce significant and undesirable Debye-Scherrer rings in the region of 3.77-5 Å. No evidence has been presented to date that show either medium to be suitable for the delivery of multi-protein complexes, membrane proteins, nucleic acids, macromolecular complexes, or viruses. Thus, there would be utility in an inert medium for the delivery of both soluble and membrane proteins, nucleic acids, macromolecular complexes, and viruses to the XFEL beam at slow flow rates.

SUMMARY OF THE INVENTION

In a first aspect, provided herein is a method for preparation of an inert crystal delivery medium, the method generally comprising the steps of: preparing an agarose solution comprising agarose, a cryoprotectant, and a first crystallization buffer; preparing a crystal solution comprising a plurality of crystals and a second crystallization buffer; and mixing the crystal solution and the agarose solution such that the plurality of crystals are suspended within the agarose solution to form an inert crystal delivery medium.

In some embodiments of the first aspect of the invention, the crystal solution is contained within a first syringe, the agarose solution is contained within a second syringe, and the first and second syringe are coupled to mix the crystal solution and agarose solution and, thereby, form the inert crystal delivery medium. In some embodiments, the cryoprotectant is provided at a concentration sufficient to prevent formation of ice. In some embodiments, the first crystallization buffer of the agarose solution and the second crystallization buffer of the crystal solution are the same crystallization buffer. In some embodiments, the crystal delivery medium comprises 5-10% agarose.

In some embodiments of the first aspect of the invention, the plurality of crystals comprise at least one of a soluble protein, a membrane protein, a soluble protein complex, a membrane protein complex, a complex comprising soluble and membrane proteins, a nucleic acid, a virus, a macromolecule, and mixtures thereof. In one embodiment the crystals are protein crystals. In some embodiments, the crystal delivery medium comprises crystals of between 100 nm to 40 µm in size. In some embodiments, the crystals are between 1 to 10 µm in size.

In a second aspect, provided herein is a crystal delivery medium, the medium comprising: crystals; agarose; a cryoprotectant; and a crystallization buffer.

In some embodiments of the second aspect of the invention, the crystals comprise at least one of a soluble protein, a membrane protein, a soluble protein complex, a membrane protein complex, a complex comprising soluble and membrane proteins, a nucleic acid, a virus, a macromolecule, and mixtures thereof. In one embodiment the crystals are protein crystals. In some embodiments, the crystal delivery medium comprises crystals of between 100 nm to 40 µm in size. In some embodiments, the crystals are between 1 to 10 µm in size.

In some embodiments of the second aspect of the invention, the cryoprotectant is provided at a concentration sufficient to prevent formation of ice. In some embodiments, the cryoprotectant is a polyethylene glycol. In some embodiments, the cryoprotectant is a sugar. In some embodiments, the crystal delivery medium comprises 5-10% agarose.

In a third aspect, provided herein is a system for preparation of a crystal delivery medium for serial femtosecond crystallography, the system comprising: crystals; an agarose solution; and a means for mixing the crystals into the agarose solution.

In some embodiments of the third aspect of the invention, the crystals comprise at least one of a soluble protein, a membrane protein, a soluble protein complex, a membrane protein complex, a complex comprising soluble and membrane proteins, a nucleic acid, a virus, a macromolecule, and mixtures thereof. In one embodiment the crystals are protein crystals. In some embodiments, the crystal delivery medium comprises crystals of between 100 nm to 40 µm in size. In some embodiments, the crystals are between 1 to 10 µm in size.

In some embodiments of the third aspect, the agarose solution comprises agarose, a crystallization buffer, and a suitable amount of cryoprotectant such that no ice is formed.

BRIEF DESCRIPTION OF DRAWINGS

The patent or patent application file contains at least one drawing in color. Copies of this patent or patent application publication with color drawings will be provided by the Office upon request and payment of the necessary fee.

DETAILED DESCRIPTION OF THE INVENTION

Figures 1A, 1B, 1C, 1D:
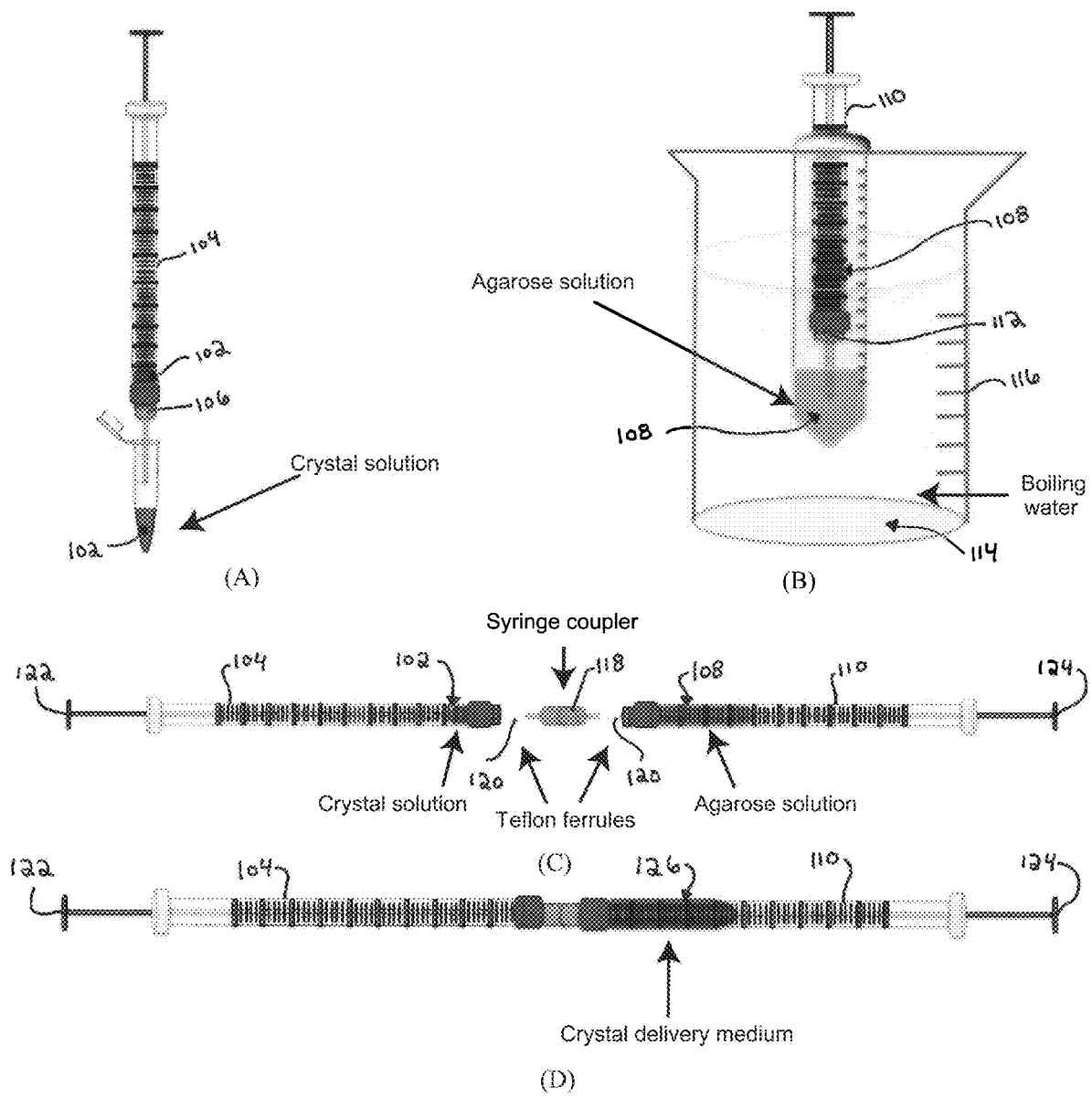
FIGS. 1A-1D are diagrams showing how the crystals are embedded into the agarose medium and the system 100 for preparation of a crystal delivery medium. (A) A dense pellet of crystals is drawn up into a syringe, (B) the agarose solution (contained in a 15 ml centrifuge tube) is submerged in boiling water until the agarose dissolves, the liquid agarose is drawn up into a warmed syringe and the agarose is allowed to gel and equilibrate to room temperature, (C) the crystals and agarose syringe are connected by a syringe coupler and (D) using the syringe coupler, the crystals are embedded throughout the agarose by moving the plungers back and forth.
Figure 2A:
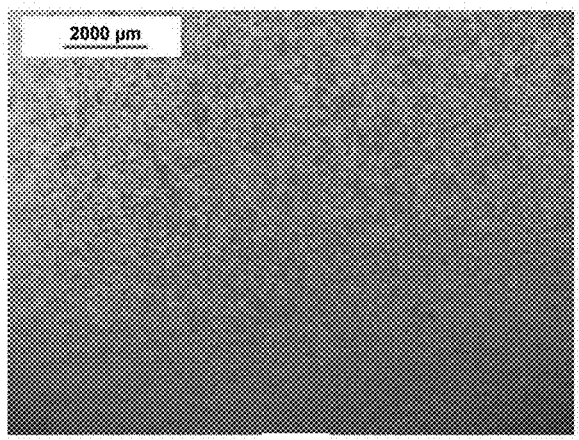
FIGS. 2A-2D. Protein crystals before and after mixing with agarose. (A) phycocyanin microcrystals, (B) phycocyanin crystals after mixing with agarose (birefringent), (C) photosystem II microcrystals (birefringent), (D) photosystem II crystals after mixing with agarose (birefringent).
Figure 2B:
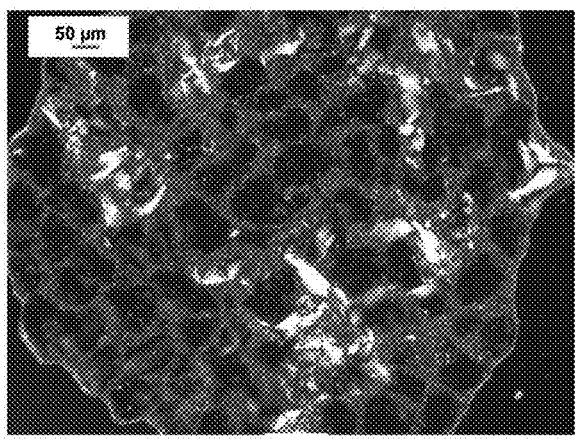
Figure 2C:
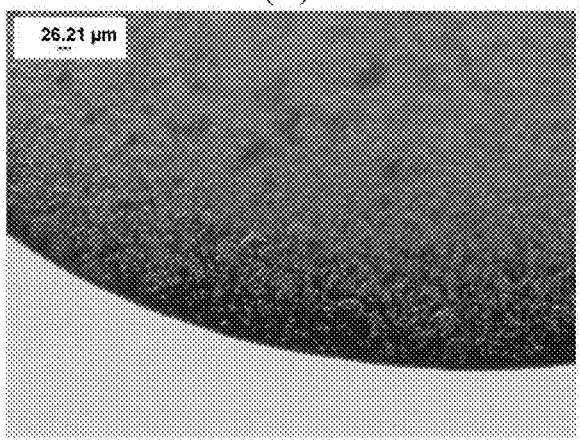
Figure 2D:
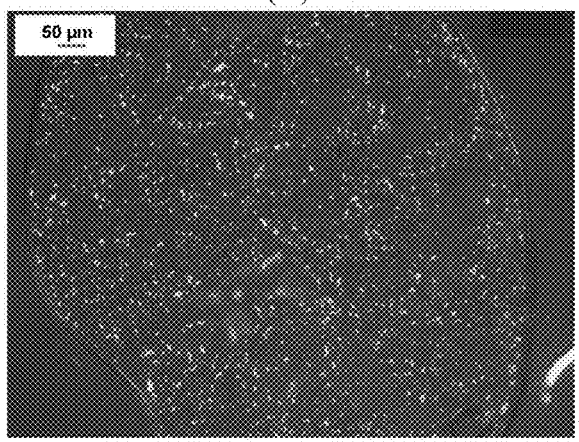

The present disclosure describes an inert crystal delivery medium based on agarose, and system and method of preparation, for serial femtosecond crystallography (SFX). Crystals grown via any crystallization methods can be embedded into agarose prior to injection for SFX experiments.

The medium, system and method as disclosed herein can provide a delivery medium for crystal injection for SFX experiments. It delivers a stable extrusion stream compatible with a variety of crystal growth and preparation methods for use in injection streams for SFX experiments.

The crystal delivery medium may be used by any means or apparatus known in the art, through which the crystals contained within the crystal delivery medium may be introduced into an X-ray source such that a diffraction patter may be measured. The crystal delivery medium has utility to be used in conjunction with X-ray free electron lasers, synchrotron radiation facilities, and the like. In one embodiment, the crystal delivery medium may be used with the lipidic cubic phase (LCP) injection system as described in U.S. patent application Ser. No. 14/780,766, incorporated herein by reference.

The medium as disclosed in the present application comprises agarose, an appropriate cryoprotectant, a collection of crystals, and a crystallization buffer from which the crystals were grown. The crystal delivery medium as disclosed is configured such that it will provide a viscous liquid stream of crystals for macromolecule X-ray structure solution. In one embodiment, crystals may be provided in the crystal delivery medium at a concentration between 1 crystal to $1\times10^{15}$ crystals per milliliter. In another embodiment, the crystals are present in the crystal delivery medium at a concentration of $1\times10^{10}$ to $1\times10^{12}$ crystals per milliliter.

As used herein, "crystal solution" may refer to the composition comprising a collection of crystals and the crystallization buffer from which they were grown.

As used herein, "crystals" may refer to protein, nucleic acid, macromolecular complex, or virus crystals composed of highly ordered and symmetrically packed macromolecules. Proteins used in the crystallization of the present disclosure may include, but are not limited to, soluble proteins, membrane proteins, soluble protein complexes, membrane protein complexes, complexes comprising soluble and membrane proteins, and mixtures thereof.

Crystals to be used in the crystal delivery medium described herein may be characterized by any crystal morphology. A collection of crystals to be used in the crystal delivery medium may be nanocrystals or microcrystals. As used herein "nanocrystals" may refer to crystals having at least one dimension less than 100 nanometers. As used herein "microcrystals" may refer to crystals which may be viewed under a microscope, typically having at least one dimension between 1 to 50 μm. In one embodiment crystals are between 100 nm to 40 μm. In one embodiment the crystals are between 0.5 to 20 μm in size. In another embodiment, the crystals are between 1 to 10 μm in size.

As used herein, "crystallization buffer" may refer to any combination of salts, buffers, precipitates, solvents, and additives in which crystals are grown. It is well established in the art that crystals may be grown in a wide variety and combination of crystallization buffers encompassing a wide variety of components. The present medium is capable of being used in combination with any crystallization buffer known in the art, or any crystallization buffer comprising any combination of salts, buffers precipitates and additives which is capable of growing crystals of a macromolecule or macromolecular complex. Common crystallization buffer components may include, but are not limited to, salts, buffers, precipitates, solvents, organic acids, sugars, polymer molecules, ligands, additives, and mixtures thereof. The term crystallization buffer is not limiting to any one particular, known, or recorded buffer system. It can be appreciated by one of skill in the art that different macromolecules exhibit different grown patterns in different crystallization buffers and as such the present disclosure can accommodate a variety of crystallization buffers. By matching the components and composition of the crystallization buffer in the liquid agarose solution to the crystallization buffer of the crystal solution, the crystals should not be disrupted or disturbed upon mixing with the agarose buffer. In one embodiment the crystallization buffer in the crystal solution is the same as the crystallization buffer in the agarose solution. In another embodiment, the crystallization buffer in the crystal solution is different than the crystallization buffer in the agarose solution, provided that the crystals do not dissolve when mixed into the agarose solution.

A large variety of different precipitants commonly used for crystallization are compatible with the agarose crystal delivery medium, including high salt concentrations as well as polyethylene glycols (PEGs). Examples include, but are not limited to, 1 M NaCl, 1.25 M ammonium sulfate, 0.2 M CaCl2 and a large range of PEGs commonly used for crystallization (PEG 400-8000 at a concentration of up to about 40%). The stability of the agarose-based stream is a function of its specific viscoelastic and surface-tension properties; notable variations are observed over the range of crystal compositions tested. Furthermore, agarose is also compatible with organic precipitants such as 2-methyl-2,4-pentanediol (MPD).

As used herein, "cryoprotectant" may refer to any salt, solution, precipitant, buffer or additive capable of stabilizing a crystal solution or crystal preparation such that is protected from distortions or breakage due to temperature changes or changes in the hydration of the crystal. A suitable amount of cryoprotectant, when combined in the crystal delivery medium or with the crystallization buffer, will cool to cryogenic temperature without ice formation and damage to the crystal. Common cryoprotectants include, but are not limited to polyethylene glycols (PEGs), glycerol, ethylene glycol, non-volatile organics, osmolytes, polyols, polymers, solvents, sugars, salts, oils, and mixtures thereof.

Agarose is a versatile polysaccharide polymer. Extracted from seaweed, agarose dissolves in water at high temperatures (above 85° C.) and forms a network of helical strands upon cooling, resulting in the formation of a gel material (Arnott et al., 1974). The concentration of agarose in the delivery medium can be tuned to control and adjust the viscosity of the medium. In one embodiment agarose is present at 2-20% in the delivery medium. In another embodiment, agarose is present at 4-15%. In another embodiment, agarose is present at 5-10% in the final crystal delivery medium. In another embodiment, the agarose is present at 5.5-7.5% in the crystal delivery medium.

As used herein, "agarose solution" may refer to a composition comprising agarose, a cryoprotectant, and a crystallization buffer. The cryoprotectant may be selected from any known or suitable cryoprotectant in the art including, but not limited to, polyethylene glycols (PEGs), glycerol, ethylene glycol, non-volatile organics, osmolytes, polyols, polymers, solvents, sugars, salts, oils, and mixtures thereof. The crystallization buffer may be selected such that it matches the composition of the crystallization buffer in which the crystals have been grown. It will be appreciated by one of skill in the art that the agarose and cryoprotectant may need to be provided at a higher concentration in the agarose solution than is desired in the final crystal delivery medium, as the agarose and cryoprotectant will be slightly diluted when mixed with the crystal solution. As an example, in one embodiment an agarose solution comprising 7-9% agarose may be used to generate a crystal delivery medium comprising 5.6-7.2% agarose.

The crystal delivery medium of the present disclosure can be tuned and adapted in regards to the concentration of agarose and the concentration and selection of cryoprotectant, such that the final crystal delivery medium is at the desired viscosity for use in injectors for serial femtosecond crystallography. Due to the variety of crystallization buffers used and the vastly different electrostatic properties of various proteins, nucleic acids, macromolecules, viruses and the like, one of skill in the art will appreciate that different cryoprotectants and concentrations of agarose will need to be used to ensure a consistent viscosity of the final crystal delivery medium and prevent freezing of the crystals and introduction of ice into the medium. The final viscosity of the crystal deliver medium should be such that it will form a stable jet or stream through an injector nozzle rather than forming a droplet. The variability in the crystal composition, crystallization buffer, cryoprotectant and temperature of the data collection experiment will change the viscosity requirements of the delivery medium. It may also be necessary to change or tune the volume of each solution to be mixed or the ratio of the two solutions in the final medium. In one embodiment, the crystal solution and agarose solution are mixed at 4 parts agarose solution to 1 part crystal solution.

The crystal delivery medium of the present disclosure is generally inert, and demonstrates very little background interference or scattering with currently established serial femtosecond crystallography methods. Overall, the background scattering from the agarose medium is roughly 2.3 times less than that from LCP in the diffuse-ring regions. Furthermore, LCP scatters strongly at very low resolution (>30 Å), while the low-angle scattering is very low in the agarose medium owing to the lack of long-range order and thus is ideal for large unit cells (Lawrence et al., 2015). Indeed, LCP (Weierstall et al., 2014; Liu et al., 2013), mineral oil-based grease (Sugahara et al., 2015) and petroleum jelly (Botha et al., 2015) all result in higher background scattering than agarose, especially at low resolution (below ~30 Å). Each of the media also produces diffuse scattering and/or Debye-Scherrer rings at 4-5 Å for LCP, 4-5 and 14 Å for mineral oil-based grease and 4.2 and 3.77 Å for petroleum jelly. Without being bound to one particular concept or theory, the low background of agarose might be explained considering that it is composed of 80-98% water and 2-20% agarose, compared with 50% water and 50% lipids in LCP and 100% oil in grease or petroleum jelly.

Referring to FIG. 1, a method according to one embodiment of the present application is provided. A prepared crystal solution 102 is drawn into a first syringe 104 through a needle 106 connected to the first syringe 104. The crystal solution 102 is prepare by any means known in the art and comprises a collection of crystals within a crystallization buffer in which the crystals were grown. The crystal solution 102 may comprise a collection of crystals comprising soluble proteins, membrane-bound proteins, protein complexes, nucleic acids, macromolecular complexes, viruses, and the like.

A prepared agarose solution 108 is drawn into a second syringe 110. The agarose solution 108 is prepared by mixing an appropriate quantity of agarose with an appropriate cryoprotectant and a crystallization buffer, such that the crystallization buffer matches the crystallization buffer of crystal solution 102. The agarose solution 108 is heated to melt the agarose such that the agarose solution 108 becomes a homogeneous liquid. The agarose solution may be heated by a variety of means known in the art including, but not limited to, a water bath, a heating block, a microwave, a thermocycler, or the like. In one embodiment the agarose solution 108 may be heated in boiling water 114 contained within a beaker 116. The boiling water 114 may also be contained within a free standing water bath, a sink, a basin or a heating bock. When the prepared agarose solution 108 has become a homogeneous liquid it is drawn into a second syringe 110, through a needle 112, which has first been heated such that the temperature of the second syringe 110 is substantially the same as the temperature of the liquid agarose solution 108, such that the agarose solution 108 remains a liquid and does not change temperature when it is drawn into the second syringe 110. After the agarose solution 108 has been drawn into the second syringe 110, the agarose solution 108 contained within the second syringe 110 may be allowed to cool to ambient temperature in order for the agarose solution 108 to gel.

After removal of the needles 106 and 112, the first syringe 104 and second syringe 110 are coupled via a syringe coupler 118 secured by Teflon ferrules 120. The syringe coupler 118 is configured to reversibly lock the first syringe 104 to the second syringe 110, such that the solutions contained within the first syringe 104 and second syringe 110 can exchange and be mixed between the two syringes without losing volume of either solution. The crystal solution 102 and the agarose solution 108 are exchanged between the two syringes by alternatively depressing the plunger 122 of the first syringe 104 and the plunger 124 of the second syringe 110 such that the two solutions are passed back and forth between the first syringe 104 and the second syringe 110 whereby the two solutions are mixed to form a crystal delivery medium 126. The solutions are mixed until the crystals were visually homogenously distributed in the agarose crystal delivery medium 126. In one embodiment the solutions are exchanged 0-100 times between the first syringe 104 and the second syringe 110. In another embodiment, the solutions are exchanged 20-80 times. In another embodiment, the solutions are exchanged 30-60 times.

The volume of crystal solution 102 provided in the first syringe 104 and the volume of agarose solution 108 provided in the second syringe 110 may be tuned or altered to achieve the desired viscosity and concentration of crystals in the crystal delivery medium 126. In one embodiment, the solutions are provided at 4 parts agarose solution 108 to 1 part crystal solution 102.

Referring to FIG. 1, a system 100 according to one embodiment of the present application is provided. The system for the preparation of a crystal delivery medium of the present application is comprised of a crystal solution 102, an agarose solution 108, and a means by which the two solutions may be mixed. In the embodiment presented in FIG. 1, the crystal solution 102 is contained within a first syringe 104, the agarose solution 108 is contained within a second syringe 110, and the means by which the two solutions may be mixed comprises the first syringe 104, the second syringe 110, and a syringe coupler 118. The syringe couple is configured to reversibly lock the first syringe 104 to the second syringe 110, such that the solutions contained within the first and second syringe can exchange and mix without losing volume of either solution.

Crystal delivery in agarose can be accomplished in an expansive temperature range, allowing crystallization conditions over a wide range of temperatures to be compatible with crystal delivery. Thus, agarose has the potential to be a general crystal-delivery medium for SFX for both soluble and membrane proteins. In one embodiment the agarose crystal delivery medium is compatible with crystals grown between 0 to 40° C. In another embodiment, the crystal delivery medium is compatible with crystals grown between 2 to 30° C. In another embodiment, the crystal delivery medium is compatible with crystals grown between 4 to 25° C.

The crystal delivery medium may be used in any injection system or data collection method known in the art. The use of the agarose crystal delivery medium in an injection stream may use a high-velocity inert-gas (nitrogen or helium) sheath to center and stabilize the emerging crystal jet extrusion, as is established in the art (Weierstall et al., 2014). This stability is used to reliably align the agarose stream with the XFEL beam axis. The use of an agarose crystal deliver medium may result in a higher stability of the stream in vacuum compared with the ambient-pressure setup in the helium atmosphere. The lower stability of the stream at atmospheric pressure is presumably owing to a turbulent boundary layer at the interface between the inert-gas sheath stream and the surrounding ambient-pressure inert gas. Furthermore, the background is higher in the He atmosphere compared with the vacuum setup. For these reasons, vacuum operation of the stream using the agarose crystal delivery medium may be preferred when freezing can be avoided by the addition of PEG, glycerol or other cryoprotectants.

The present invention has been described in terms of one or more preferred embodiments, and it should be appreciated that many equivalents, alternatives, variations, and modifications, aside from those expressly stated, are possible and within the scope of the invention.

EXAMPLE 1

The embodiment described here demonstrates that crystals of complex membrane proteins, such as the photosynthetic protein complexes photosystem I (PSI) and photosystem II (PSII), can be delivered in an agarose stream for SFX and structure solution. To test whether agarose could be used to deliver crystals of large, multi-protein complexes, phycocyanin (PC) was chosen as a model system. PC is a cyanobacterial antennae protein, part of the light-harvesting complex, which channels excitation energy to PSII, subsequently driving charge separation across the thylakoid membrane, the membrane that contains PSI and PSII. The PC complex forms a disc-like trimer in which each monomer is composed of two subunits, α and β (Schirmer et al., 1985).

1.1. Protein Purification and Crystallization

PC was isolated from Thermosynechococcus elongatus. Briefly, the protein was obtained by disrupting a concentrated suspension of cells using a microfluidizer at 124 MPa. The resulting suspension was further purified by ultracentrifugation at 50,000 g for 1 hour, in which large particles and aggregates were separated from the supernatant. The supernatant was then concentrated using Amicon Ultra-15 spin filters (Millipore, 100 kDa cutoff), in which most small cytosolic proteins are separated as they flow through the filters. PC was crystallized by free-interface diffusion as described by Kupitz et al. (2014) for PSII (Saridakis & Chayen, 2003). The crystallization buffer solution comprising 1.0 M ammonium sulfate, 40 mM 2-(N-morpholino)ethanesulfonic acid (MES) pH 6.4 was added drop-wise at 1 ml s$^{-1}$ to an equal volume of protein solution (15 mg ml$^{-1}$). Crystals of 1-5 µm in size formed after 1 day and were confirmed via second-order nonlinear imaging of chiral crystals (Kissick et al., 2011). Prior to embedding the crystals in the agarose medium, the crystals were filtered through a 10 mm stainless-steel filter. PSI was isolated and purified in principle as described by Fromme & Witt (1998) and Hunter & Fromme (2011) using crystallization at low ionic strength as the last purification step. The crystals were stabilized in a low ionic strength crystallization buffer that comprised 5 mM MES pH 6.4, 0.02% β-dodecylmaltoside (β-DDM). PSII was isolated and purified as described by Kupitz et al. (2014). The concentrated protein was subjected to a series of batch crystallization steps with decreasing concentrations of precipitant, as described in Kupitz et al. (2014). The crystals were permitted to grow for 24 h and crystal growth was then terminated by the removal of the supernatant and the addition of crystallization buffer containing low salt (100 mM 1,4-piperazinediethanesulfonic acid pH 7.0, 5 mM CaCl2, 10 mM tocopherol, 20% PEG 2000).

1.2. Preparation of the Agarose and Embedding of Crystals Into the Viscous Medium A solution of 5.6% (w/v) agarose and 30% glycerol was determined to form a stable extrusion stream. In order to obtain these conditions after mixing, 7% (w/v) ultralow-melt agarose (Sigma-Aldrich, catalog No. A5030) was dissolved in a solution of 30% glycerol and the crystallization buffer in a 15 ml centrifuge tube and submerged in a water bath filled with boiling water for 30 min. To draw up the agarose into a 100 ml syringe (Hamilton, Model 1710), the syringe was warmed by drawing up and quickly ejecting boiling water 10-15 times (to ensure the integrity of the syringe, we avoided dipping more than the needle in solutions at temperatures higher than 80° C.).

The agarose was then drawn up from a 15 ml centrifugation tube that remained submerged in the water bath. For PC, the agarose was dissolved in 600 ml glycerol and 1.4 ml of crystallization buffer comprising 15% PEG 2000, 30 mM MgCl2, 75 mM HEPES pH 7.0. For PSII, the agarose was dissolved in 600 ml glycerol and 1.4 ml of crystallization buffer comprising 100 mM PIPES pH 7.0, 5 mM CaCl2, 16% (w/w) PEG 2000. For PSI, the agarose was dissolved in 1.4 ml of crystallization buffer comprising 5 mM MES pH 6.4, 0.02% β-DDM, and 600 ml 2.0M sucrose. In the case of data collected at helium ambient pressure, 2 ml 5 mM MES pH 6.4, 0.02% β-DDM was used. 20 µl of the boiling hot agarose solution pertaining to the protein system was drawn up into a syringe. The agarose was allowed to equilibrate to room temperature for approximately 20 min before 5 µl protein crystals were mixed throughout the agarose using a syringe coupler (Cheng et al., 1998); at least 40 syringe-mixing exchanges were performed or until the crystals were visually homogenously distributed in the agarose medium.

1.3. Data Collection

Data were collected using the CXI instrument at the Linac Coherent Light Source (LCLS) at SLAC (Boutet & Williams, 2010). A continuous stream of agarose with crystals embedded was extruded from a 50 µm capillary into the X-ray interaction region using the LCP injector (Weierstall et al., 2014) at a flow rate of 160 nl min$^{-1}$.

TABLE 1

Phycocyanin data statistics
Values in parentheses are for the highest shell

| | |
|---|---|
| Wavelength (Å) | 1.33 |
| Space group | P6$_3$ |
| Resolution (Å) | 29.5-2.5 (2.55-2.50) |
| Unit-cell parameters (Å, °) | a = b = 153.4, c = 39.6, $\alpha = \beta = 90, \gamma = 120$ |
| No. of crystal hits | 41100 |
| No. of indexed patterns | 14143 |
| Duration of data collection (min) | 72 |
| Unique reflections | 18908 |
| Reflections used in refinement | 18871 |
| $<I/\sigma(I)>$ | 3.2 (0.83) |
| Multiplicity | 250.67 (12.5) |
| CC* | 0.971 (0.487) |
| Rwork/Rfree (%) | 18.7 (32.7)/25.5 (35.5) |
| Completeness (%) | 99.82 |
| Average B factor (Å$^2$) | 38.34 |

1.4. Data Processing

During 6 hours of protein crystal screening experiments at LCLS, diffraction patterns were collected from different protein crystals (PC, PSI and PSII). PC was chosen as a model system and a complete data set was collected from PC crystals delivered in agarose medium in ~72 min. The 513,848 detector readouts were background-corrected and the hits were filtered out using Cheetah (Barty et al., 2014), yielding 41,100 diffraction patterns that contained 25 or more Bragg spots (an average hit rate of 8%). 14,143 patterns were indexed (i.e. an indexing yield of 34%) and integrated using CrystFEL (White et al., 2012; Kirian et al., 2011) with a hexagonal lattice type with unit-cell parameters a=b=153.4, c=39.6 Å (see Table 1). The merohedral space group of the crystals, P6$_3$, exhibited an indexing ambiguity which was resolved by ambigator, an implementation within CrystFEL of an algorithm related to that described by Brehm & Diederichs (2014). The resolution was cutoff at 2.5 Å based on the multiplicity and the CC* value (Karplus & Diederichs, 2012; see Table 1).

The merged data set (truncated at 2.5 Å resolution) was phased by molecular replacement (MR) using phenix.phaser (McCoy, 2007) with PDB entry 4GY3 as the search model (after removing waters and ligands). The MR model was first refined using a segmented rigid-body protocol in which each subunit was considered as a rigid entity using phenix.refine. A total of ten cycles of positional, individual B-factor refinement, including two cycles of simulated-annealing refinement, were then performed. In this step, water molecules were added and refined using phenix.refine at 2.5 Å resolution. The refined structure resulted in an R-work of 18.7% and an R-free of 25.5% (see Table 1). In order to demonstrate that agarose is a suitable delivery medium for SFX data collection from soluble proteins and various membrane proteins, we have also provided diffraction patterns from PSI and PSII (see FIG. 8 and FIG. 9).

Results

Figures 6A, 6B:
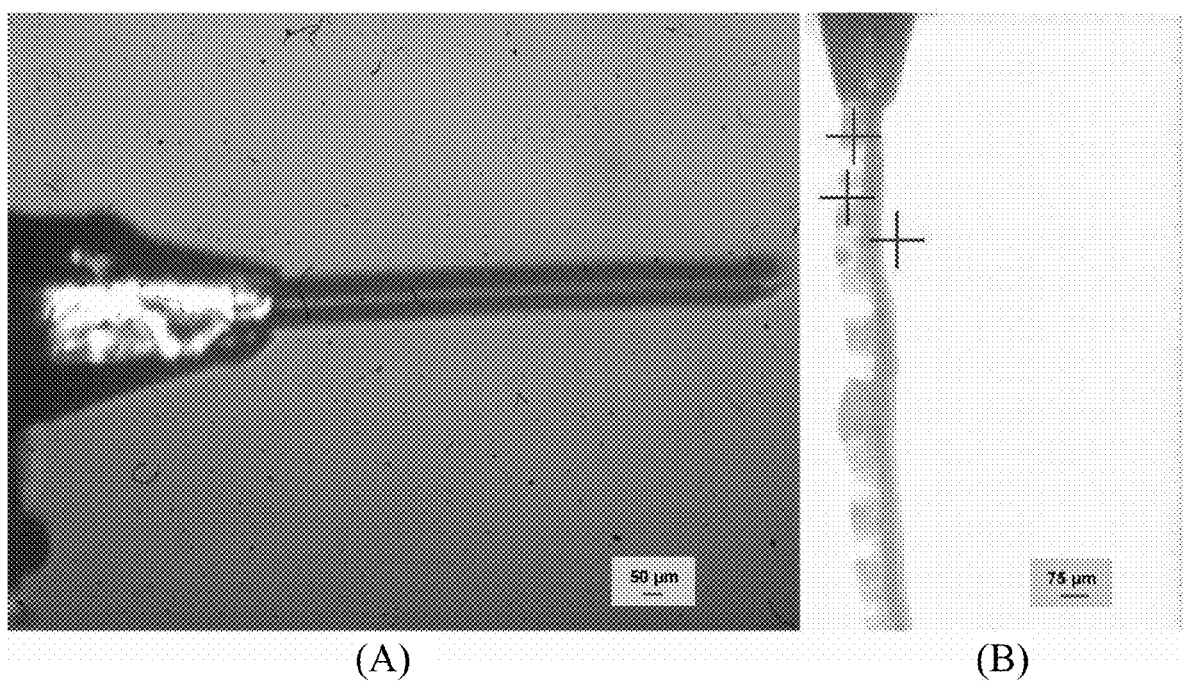
FIGS. 6A-6B show the agarose stream extrusion. (A) Agarose stream with no embedded crystals extruded in vacuum in a test chamber. (B) Agarose stream with embedded crystals extruded in vacuum in the Coherent X-ray Imaging instrument chamber.
Figure 7A:
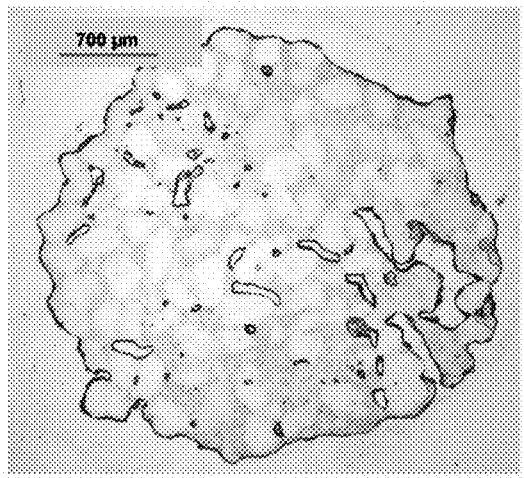
FIGS. 7A-7F show a visual characterization of PC and PSII embedded in agarose. (A) Bright field image of PC in agarose, (B) second order non-linear imaging of chiral crystals of PC in agarose, (C) ultraviolet two-photon excited fluorescence of PC microcrystals, (D) bright field image of PSII in agarose, (E) second order of non-linear imaging of chiral crystals of PSII, (F) ultraviolet two-photon excited fluorescence of PSII.
Figure 7B:
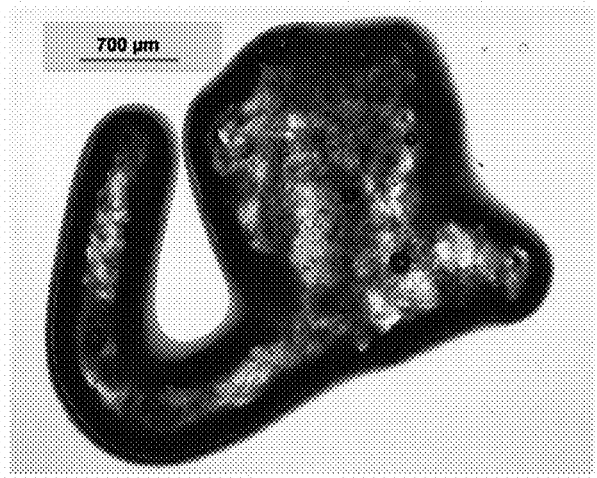
Figure 7C:
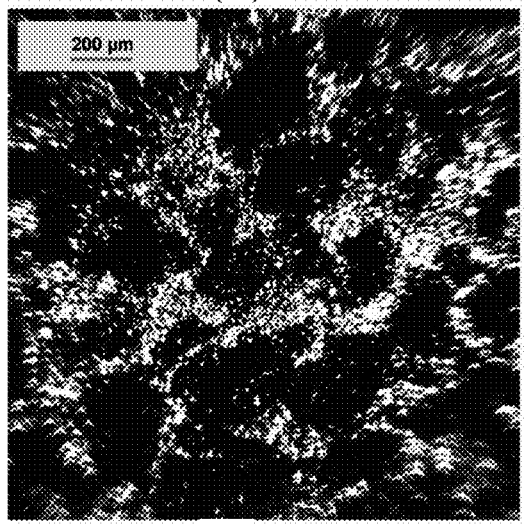
Figure 7D:
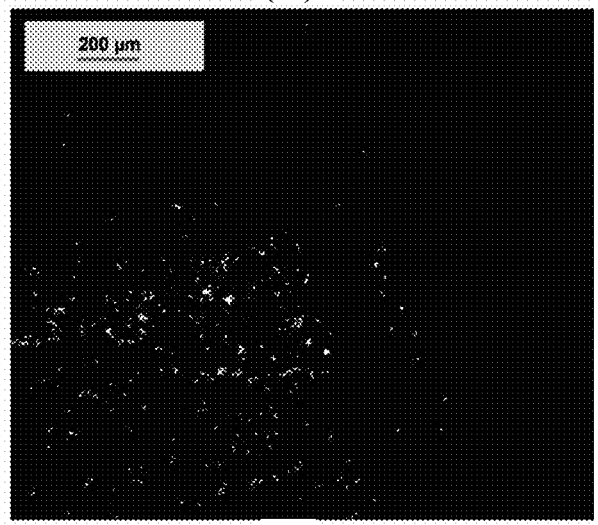
Figure 7E:
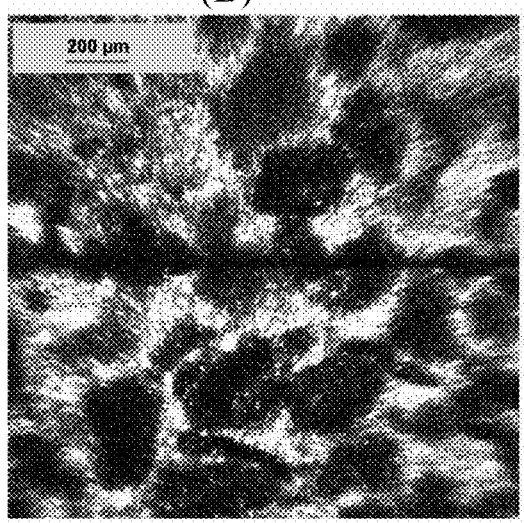
Figure 7F:
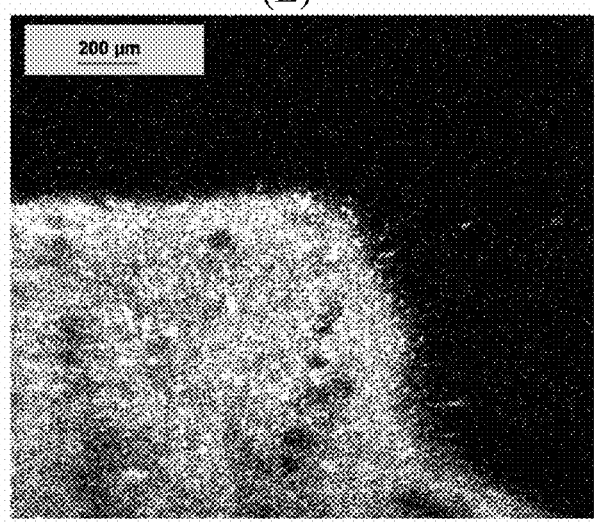

For a viscous medium to be suitable for SFX, three primary requirements must be met: the medium must maintain crystal integrity, must form a stable and continuous stream and the diffraction from the medium should produce minimal background scattering. Several viscous media were tested in order to investigate their potential as a general viscous, non-Newtonian carrying medium, including tapioca corn starch, gelatin, silica hydrogel, polyacrylamide, polyvinyl alcohol and poly(ethylene oxide). None of these media established stable streams. Initial tests using agarose as a crystal-delivery medium showed signs of dehydration in vacuum, leading to the formation of ice as detected by X-ray diffraction. To prevent freezing, we tested several potential cryoprotectants for crystal delivery in high vacuum. From those screened, we narrowed our selection to glycerol, which also increased the viscosity of the agarose stream, a welcome side effect that makes extrusion more reliable. Different concentrations of agarose and glycerol were screened to test the extrusion conditions and 5.6% agarose dissolved in 30% glycerol was found to be a suitable embodiment of the medium because it formed a stable, continuous stream and no ice-crystal diffraction artifacts were observed (FIG. 6).

Three ways were explored to embed the crystals into the agarose medium: (i) the growth of crystals in agarose, (ii) simple manual mixing on a glass slide (as has been used for the oil-based grease method; Sugahara et al., 2015) and (iii) the use of a syringe setup (FIG. 1), which was originally developed for the crystallization of proteins in LCP (Cheng et al., 1998; Caffrey & Cherezov, 2009).

The growth of crystals in agarose has been described in the literature as a method to slow down crystal growth and to counteract effects such as sedimentation and convection that influence the crystallization process under gravity (Biertümpfel et al., 2002). We first investigated the growth of PC crystals in agarose. Owing to the large size of PC, its diffusion constant is very low and crystal growth in agarose is very slow, leading to the formation of few nuclei. Furthermore, no nucleation occurred in agarose in the presence of 30% glycerol even at very high protein concentrations (>20 mg ml$^{-1}$). Although PC could not be crystallized directly in the gel owing to its large size and low diffusion constant, other proteins might be suitable for crystal formation inside the agarose gel as demonstrated previously (Garcia-Ruiz et al., 2001; Lorber et al., 2009).

While the growth of crystals of PC in agarose was very difficult, we succeeded in embedding pre-grown crystals into the agarose medium, which allowed a full SFX data set to be collected from PC crystals delivered in agarose (FIG. 7). The mixing of pre-formed crystals is therefore suggested as one embodiment of the method of crystal delivery in the agarose stream, as it does not depend on the size of the protein and allows pre-grown crystals to be delivered to the XFEL beam. However, simple mixing of crystals with agarose leads to an inhomogeneous distribution of crystals and further problems, including partial drying of crystals, the formation of crystals of salt or other precipitants and the loss of protein crystals during transfer to the injector crystal reservoir. A syringe setup for embedding crystals into the agarose medium has been designed, as shown in FIG. 1. In order to stabilize the crystals, the agarose solution was prepared in the crystallization buffer corresponding to each of the proteins. The agarose was dissolved by vortex mixing the crystallization buffer and glycerol (for sample delivery in vacuum) with the agarose powder in a 15 ml centrifuge tube. The tube was then submerged in a water bath of boiling water for approximately 30 min. A syringe was then warmed by drawing up boiling water from the water bath through the syringe and quickly ejecting it 10-15 times. With the centrifuge tube submerged in boiling water, 20 ml agarose was drawn up into the heated syringe and allowed to cool to ambient temperature. A second syringe was filled with 5 ml of the highly concentrated PC crystal suspension (ideally $10^{11}$ crystals per milliliter) in the crystallization buffer (the same crystallization buffer as used in the agarose preparation). The desired high crystal densities can be achieved by either sedimentation or low-speed centrifugation of the crystal suspensions prior to mixing with the agarose medium.

After the agarose had entered the gel phase in the syringe, the syringes containing agarose and the protein crystals were connected using a syringe coupler (FIG. 1; Cheng et al., 1998). The crystals were then embedded into the agarose by alternate movement of the two plungers, whereby the solutions moved back and forth between the two syringes at least 40 times (FIG. 7), leading to the embedding of the crystals in the agarose medium at a crystal density of $2 \times 10^{10}$ crystals per milliliter. Owing to the dilution caused by mixing of the agarose medium with the crystal suspension, the medium becomes less viscous, and the initial percentage of agarose must be increased to compensate for the dilution.

Figures 9A, 9B:
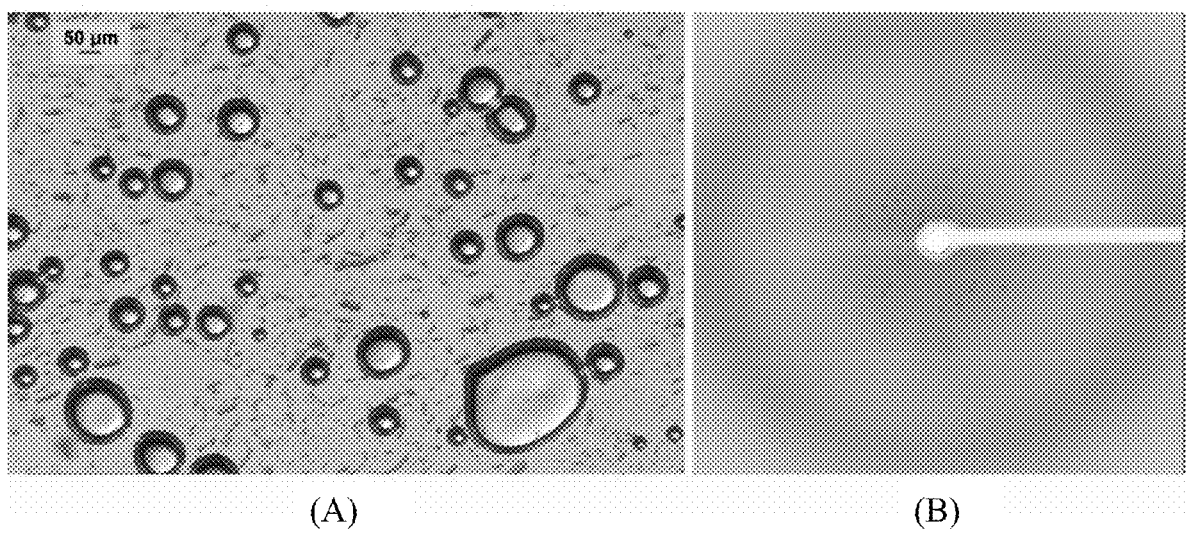
FIGS. 9A-9B show PSI embedded in agarose and delivered in a helium atmosphere. (A) Rod-like PSI crystals embedded in agarose, (B) diffraction pattern from PSI microcrystal in agarose.

The initial agarose concentration was increased to 7% agarose in order to achieve a final concentration of 5.6% after mixing with the crystals. We used the same procedure of embedding crystals of soluble model proteins such as lysozyme and the large protein—cofactor complex PC, as well as one of the largest and most complex membrane-protein complexes that has been crystallized so far: PSII (a dimer of 700 kDa containing 38 protein subunits and more than 100 cofactors). Pictures of the different crystals embedded in agarose are shown in FIG. 2, FIG. 7, and FIG. 9.

Dissolving the agarose in different precipitants in some cases decreased the viscosity. In these cases, the agarose concentration was adjusted to 9%, which increased the viscosity and the ability to form a stream. An especially challenging case for crystal delivery in agarose was the large membrane-protein complex PSI (a trimer of 1080 kDa containing 36 protein subunits and more than 300 noncovalently bound cofactors), which crystallizes at low ionic strength without the addition of any salt or precipitant [Jordan et al., 2001; Hunter & Fromme, 2011; Chapman et al., 2011; the final crystallization buffer contained 5 mM 2-(N-morpholino)ethanesulfonic acid (MES) pH 6.4 and 0.02% β-dodecylmaltoside (β-DDM) detergent]. PSI crystals dissolve in the presence of glycerol or salt and do not tolerate the addition of any organic solvents or PEGs. To prevent the freezing of the PSI crystals in the agarose stream in high vacuum, we stabilized the PSI crystals by embedding them in agarose prepared with the PSI crystallization buffer and with 0.6 M sucrose. After optimization of the crystallization buffer, PSI crystals could be embedded into agarose and delivered to the XFEL beam in agarose with suitable crystal-delivery stream stability using the crystallization buffer with sucrose described above in 9% agarose.

The agarose stream was tested using the Coherent X-ray Imaging (CXI) instrument at the Linac Coherent Light Source (LCLS) at the SLAC National Accelerator Laboratory in the vacuum-chamber setup (Boutet et al., 2012). Most of the SFX data were collected in the vacuum chamber, except for PSI, where the data shown in FIG. 9 were collected in a new ambient-pressure setup with a helium environment. The advantage of using an ambient-pressure setup is that freezing by evaporative cooling is avoided. At ambient pressure cryoprotectant is not essential as dehydration occurs much more slowly than in vacuum.

The agarose stream relies on a high-velocity inert-gas (nitrogen or helium) sheath to center and stabilize the emerging crystal jet extrusion (Weierstall et al., 2014). This stability functions to reliably align the agarose stream with the XFEL beam axis. We observed a higher stability of the stream in vacuum compared with the ambient-pressure setup in the helium atmosphere. The lower stability of the stream at atmospheric pressure is presumably owing to a turbulent boundary layer at the interface between the inert-gas sheath stream and the surrounding ambient-pressure inert gas. Furthermore, the background is higher in the He atmosphere compared with the vacuum setup. For these reasons, vacuum operation of the stream is preferred when freezing can be avoided by the addition of PEG, glycerol or other cryoprotectants. SFX data for PC and PSII were collected using the vacuum-chamber setup and SFX data for PSI and PSII were collected using the helium ambient-pressure setup as described previously.

Figure 3:
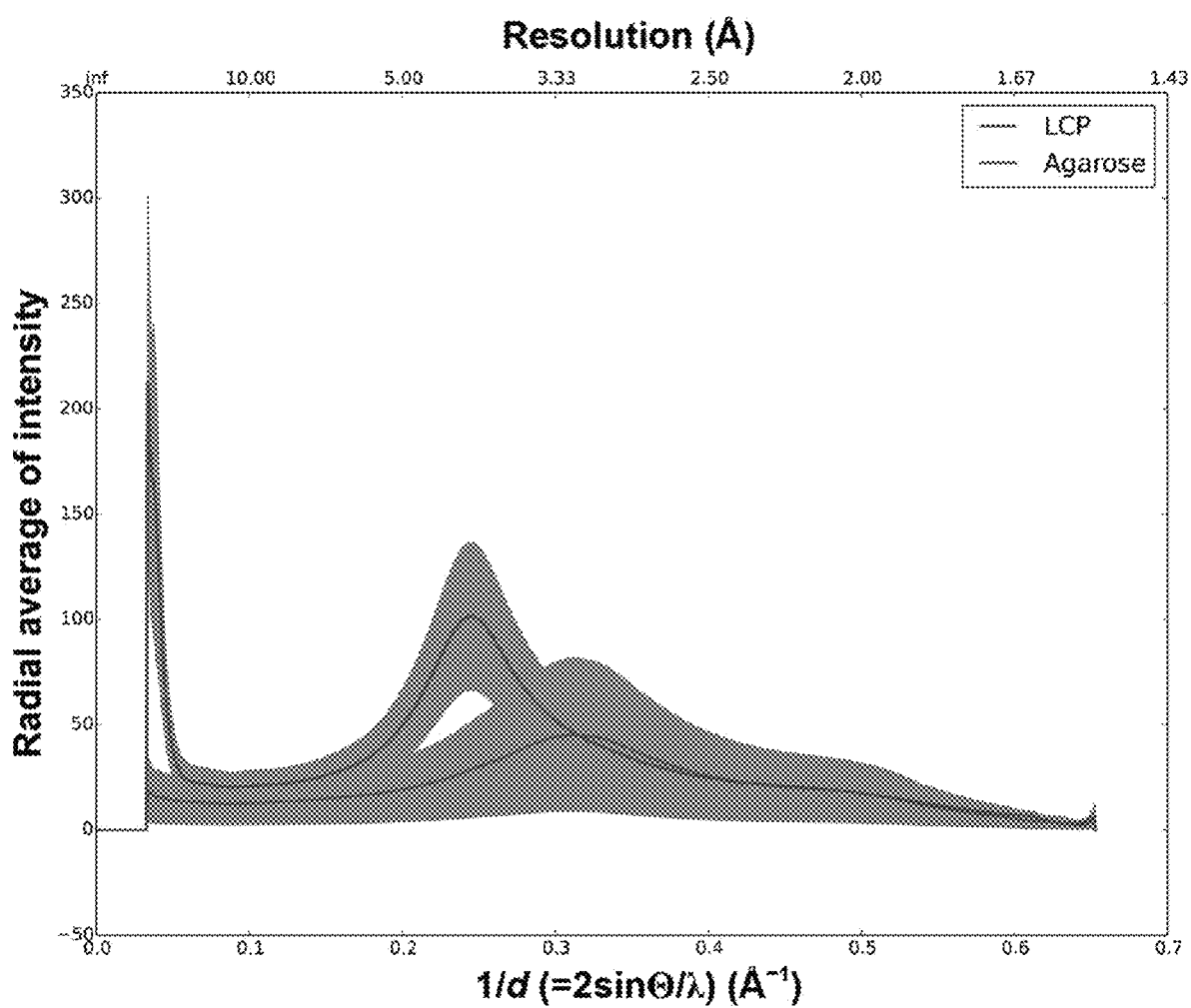
FIG. 3. Diffuse background scattering comparison between agarose and lipidic cubic phase. 1/d (x axis) is plotted against the mean radial intensity over the total number of frames used from each medium (y axis). The blue line represents the mean radial intensity for LCP medium as a function of 1/d (or resolution in Å on the second x axis). The green line represents the mean radial intensity for agarose as a function of 1/d. The error or fluctuation in the radial intensity is quantified using the mean absolute deviation for both media, which is shown as a transparent gray region.

FIG. 3 shows a comparison of the X-ray scattering from the agarose stream compared with the LCP stream. The average scattered intensity was calculated from each medium delivered in a stream of the same width (50 mm) using detector-readout events that contained no crystal diffraction. 13,902 frames were analyzed from the agarose stream data and 14 592 frames from the LCP stream data. Frames that contained no scattering from the jets/streams (owing to the jet/stream temporarily fluctuating out of the path of the X-rays) were easily recognized on the basis of their very low photon counts (~10-20 detector units) and were excluded from the mean background calculation, leaving 9147 and 8326 frames with scattering from the LCP and agarose jets, respectively. Thereby, bias from large jet/stream flow instabilities was avoided in the calculation of the mean radial intensities for each medium. To reduce the influence of shot-to-shot variations in the XFEL pulse intensities, each frame was scaled to the readings from the gas-ionization detector upstream of the vacuum chamber at the CXI. Finally, the mean radial intensities from the LCP and agarose jets were scaled to be equal at a resolution of 2 Å, where neither medium should produce a background signal. As shown in FIG. 3, a broad peak corresponding to diffuse scattering from the lipid chains of LCP can be seen at 4.5 Å resolution. Diffuse scattering from agarose can be seen in the 3.3 Å region. The gray regions represent the mean absolute deviation around the mean.

Overall, the background scattering from the agarose medium is roughly 2.3 times less than that from LCP in the diffuse-ring regions. Furthermore, LCP scatters strongly at very low resolution (>30 Å), while the low-angle scattering is very low in the agarose medium owing to the lack of long-range order and thus is ideal for large unit cells (Lawrence et al., 2015). Indeed, LCP (Weierstall et al., 2014; Liu et al., 2013), mineral oil-based grease (Sugahara et al., 2015) and petroleum jelly (Botha et al., 2015) all result in higher background scattering than agarose, especially at low resolution (below ~30 Å). Each of the media also produces diffuse scattering and/or Debye-Scherrer rings at 4-5 Å for LCP, 4-5 and 14 Å for mineral oil-based grease and 4.2 and 3.77 Å for petroleum jelly. The low background of agarose may be understood considering that it is composed of 93% water and 7% agarose, in this embodiment, compared with 50% water and 50% lipids in LCP and 100% oil in grease or petroleum jelly.

Figure 4A:
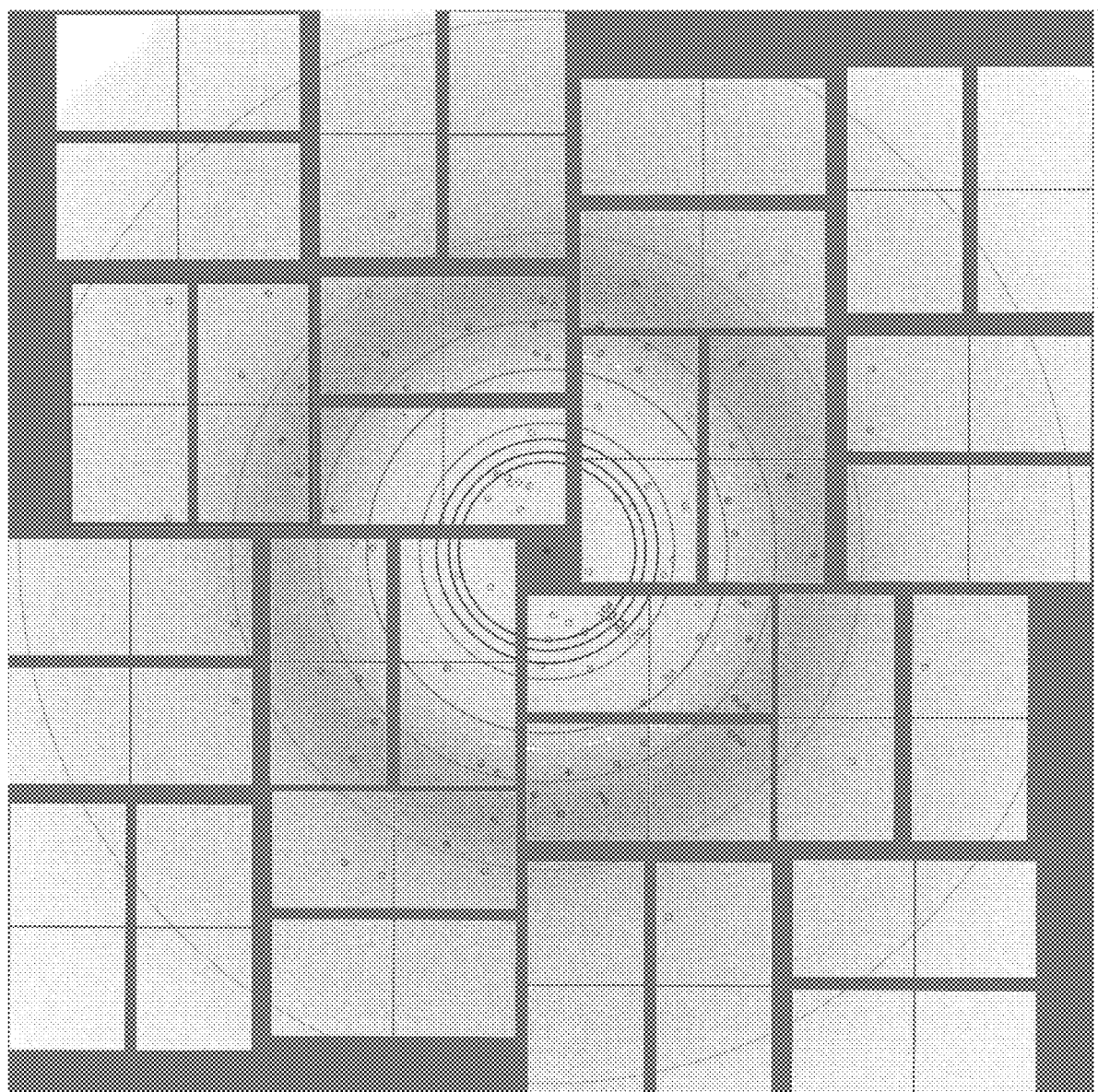
FIGS. 4A-4C show a single diffraction pattern of PC in agarose measured using the Coherent X-ray Imaging instrument at the Linac Coherent Light Source, with the red box magnified in (B) and predicted peak positions circled after indexing with CrystFEL (C).
Figure 4B:
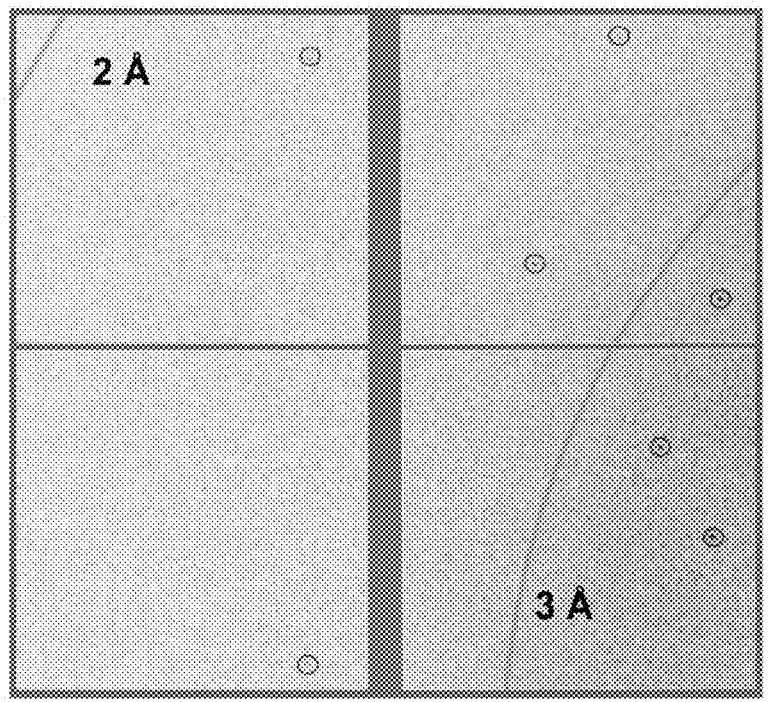
Figure 4C:
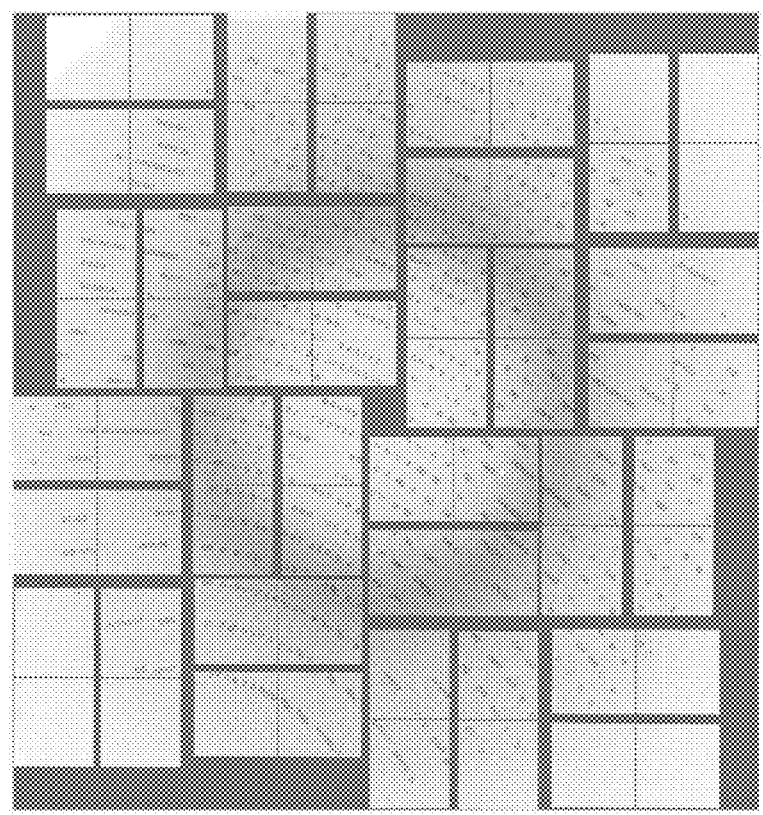
Figure 5A:
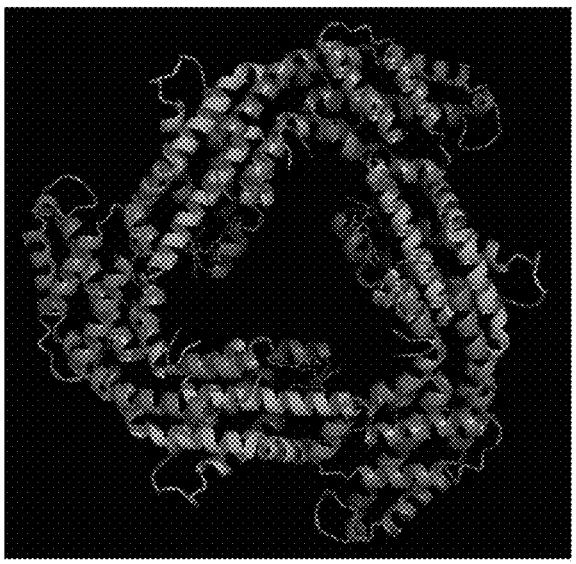
FIGS. 5A-5D show 2Fo-Fc electron-density maps of PC. (A) PC trimer composed of two subunits, α (blue) and β (green), (B) an α-helix and loop from the α subunit contoured at 2.0σ, (C) α-helices from both subunits at 1.5σ, and (D) the chromophore of PC at 1.5σ.
Figure 5B:
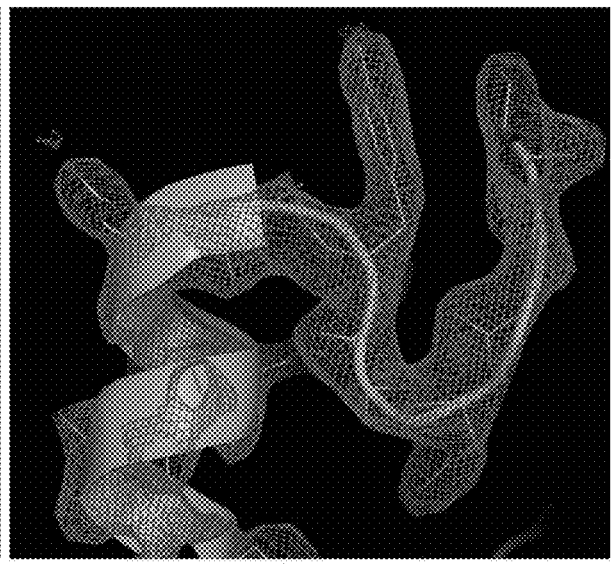
Figure 5C:
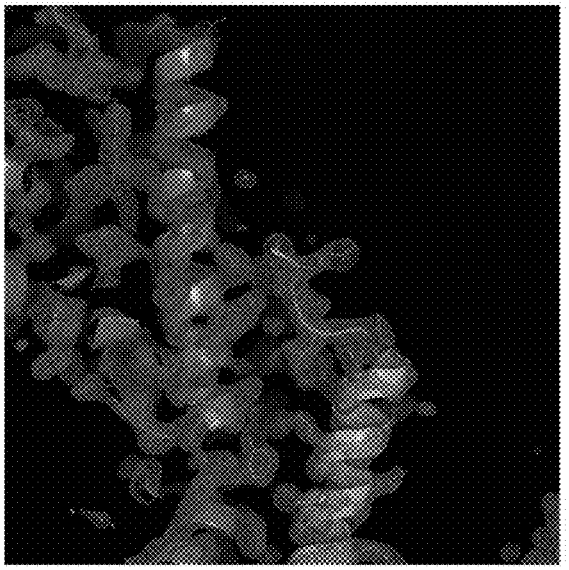
Figure 5D:
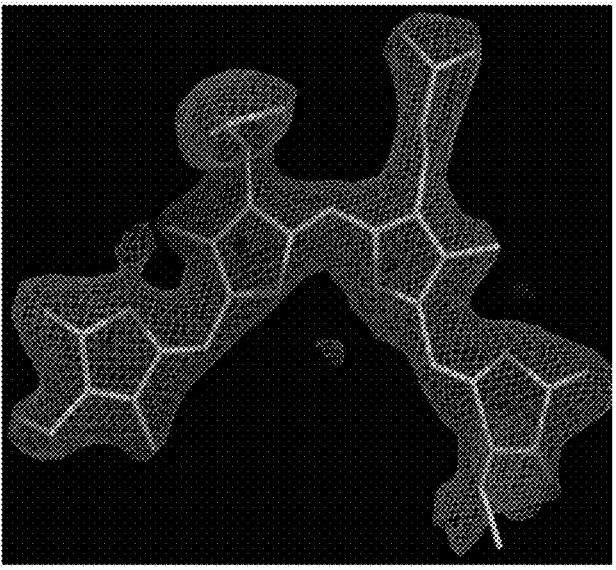
Figures 8A, 8B:
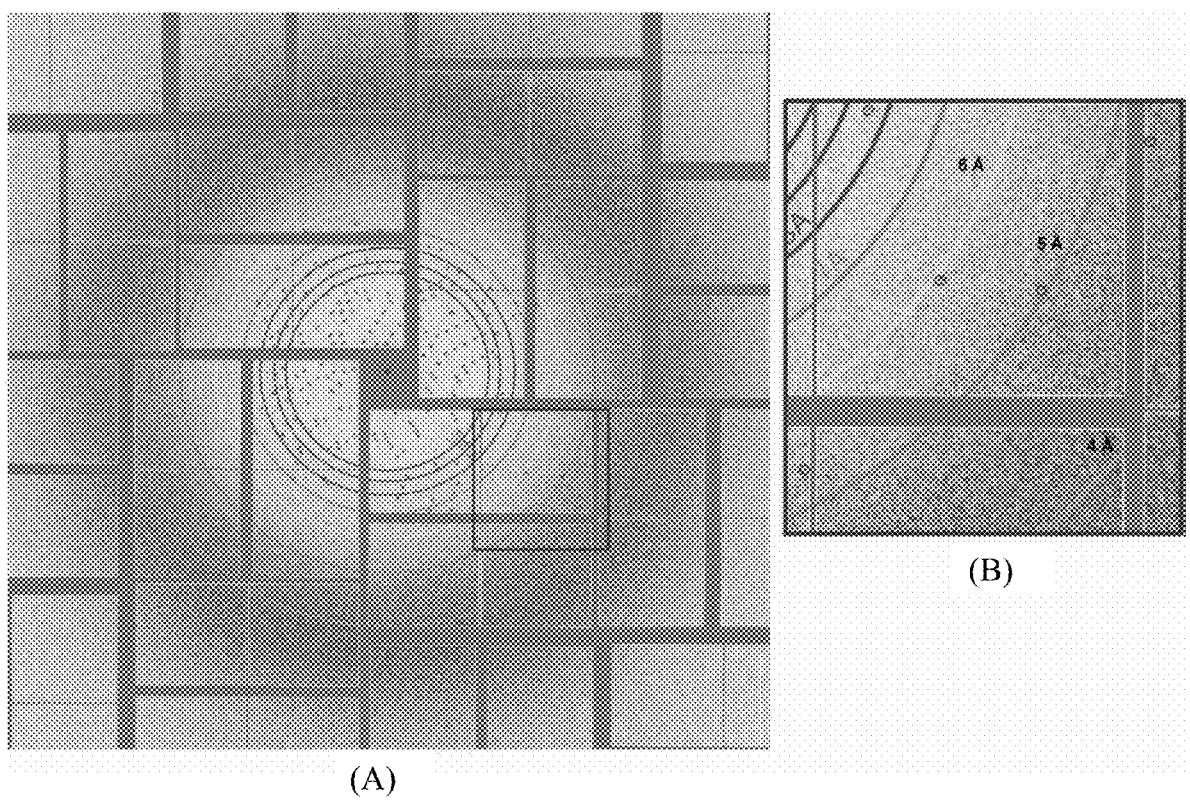
FIGS. 8A-8B show a diffraction pattern for PSII embedded in agarose and delivered in a vacuum chamber. (A) Diffraction pattern from PSII in agarose, (B) magnified subset from (A).

The time available for data collection was limited to 4 h of protein crystal screening beamtime at LCLS. A full data set for PC crystals was collected using the vacuum setup at CXI (FIGS. 3 and 4) during this time as well as a brief test run on PSII crystals. In addition, data were collected from PSII and PSI during short test runs using the ambient-pressure setup (FIGS. 3 and 4). These complexes were chosen to demonstrate that agarose is an excellent carrier medium that can be used for SFX data collection from even the largest protein complexes containing noncovalently bound cofactors (FIG. 8 and FIG. 9). The statistics of the PC data set are shown in Table 1. In 72 min of data collection, we collected 41,100 crystal hits from PC, of which 14,143 could be indexed in a hexagonal lattice with unit-cell parameters a=b=153.4, c=39.6 Å. A high multiplicity is essential for the determination of accurate structure factors by Monte Carlo integration (Kirian et al., 2010) to average out the fluctuating parameters such as pulse intensity, partiality of reflections and crystal size distribution. The PC data set showed a high overall multiplicity of 250.6 and a multiplicity of 12.5 in the highest resolution shell (2.63-2.5 Å). The structure was solved using molecular replacement and the structure was refined with final values of Rwork=18.7% and Rfree=25.2%. FIG. 5 shows the electron density map for the loops and side chains from subunit α (cyan) and subunit β (green), as well as a detailed view of phycocyanobilin, the chromophore of PC.

In comparison to the commonly used GDVN liquid jet, which consumes protein crystal suspension at 10-25 ml min$^{-1}$, the embodiment of the agarose delivery medium presented here delivers protein crystals at a flow rate of 160 nl min$^{-1}$, reducing net protein consumption by two orders of magnitude. This study has shown that the agarose medium might be suitable as a general delivery system for SFX of both soluble and membrane protein crystals and that it is compatible with a wide range of crystallization conditions as well as temperatures. The agarose jet can be used both in vacuum and at ambient pressure; so far, the stream has displayed better stability in vacuum. The agarose medium features lower X-ray scattering background compared with LCP or other viscous crystal-delivery media such as mineral oil-based grease and petroleum jelly, especially at low resolution. Thus, agarose is an ideal SFX crystal delivery medium for protein crystals with large unit cells and medium-to-low resolution limits. The agarose delivery system is a low-cost, readily available medium for sample delivery of crystals of soluble and membrane-protein complexes and is compatible with most commonly used precipitants, including various PEGs as well as high-salt conditions. This study has demonstrated that crystals can be embedded into the agarose medium post-crystallization. Furthermore, low sample consumption extends the SFX method towards protein complexes that are difficult to express and isolate in large amounts. Thus, this technique will allow structures of scarce proteins and systems that are difficult to crystallize in large quantities to be investigated by serial femtosecond crystallography.

We claim:

1. A method for preparation of an inert crystal delivery medium, the method comprising the steps of: preparing an agarose solution comprising agarose, a cryoprotectant, and a first crystallization buffer; preparing a crystal solution comprising a plurality of ordered and symmetrically packed membrane-bound protein crystals and a second crystallization buffer, wherein membrane-bound protein of the membrane-bound protein crystals is insoluble in water; and mixing the crystal solution and the agarose solution such that the plurality of membrane-bound protein crystals are suspended within the agarose solution to form an inert crystal delivery medium comprising the plurality of membrane-bound protein crystals, 5.5%-10% (w/v) agarose, the cryoprotectant, the first crystallization buffer, and the second crystallization buffer.

2. The method of claim 1, wherein the crystal solution is contained within a first syringe, the agarose solution is contained within a second syringe, and the first and second syringes are coupled to mix the crystal solution and agarose solution and, thereby, form the inert crystal delivery medium.

3. The method of claim 1, wherein the cryoprotectant is provided at a concentration sufficient to prevent formation of ice.

4. The method of claim 1 wherein the first crystallization buffer of the agarose solution and the second crystallization buffer of the crystal solution are the same crystallization buffer.

5. The method of claim 1, wherein the plurality of the membrane-bound protein crystals comprises crystals of between 100 nm to 40 μm in size.

6. The method of claim 5, wherein the crystals are between 1 to 10 μm in size.

7. A crystal delivery medium, the medium comprising:
   ordered and symmetrically packed membrane-bound protein crystals, wherein membrane-bound protein of the membrane-bound protein crystals is insoluble in water;
   5.5%-10% (w/v) agarose;
   a cryoprotectant; and
   a crystallization buffer.

8. The medium of claim 7, wherein the cryoprotectant is a polyethylene glycol.

9. The medium of claim 7, wherein the cryoprotectant is a sugar.

10. The medium of claim 7, wherein the cryoprotectant is provided at a concentration sufficient to prevent formation of ice.

11. The medium of claim 7, wherein the cryoprotectant is selected from the group consisting of polyethylene glycols, glycerol, ethylene glycol, non-volatile organics, osmolytes, polyols, sugars, oils, and mixtures thereof.

12. The medium of claim 11, wherein the cryoprotectant is selected from the group consisting of polyethylene glycols, glycerol, ethylene glycol, sugars, and mixtures thereof.

13. A system for preparation of a crystal delivery medium for serial femtosecond crystallography, the system comprising: ordered and symmetrically packed membrane-bound protein crystals, wherein the membrane-bound protein of the membrane-bound protein crystals is insoluble in water; an agarose solution comprising 5.5%-10% (w/v) agarose, a cryoprotectant, and a crystallization buffer; and a first syringe, a second syringe, and a syringe coupler for mixing the membrane protein crystals into the agarose solution.

14. The system of claim 13, wherein the cryoprotectant is provided at a concentration sufficient to prevent formation of ice.

* * * * *

UNITED STATES PATENT AND TRADEMARK OFFICE
CERTIFICATE OF CORRECTION

PATENT NO. : 10,775,322 B2
APPLICATION NO. : 15/183149
DATED : September 15, 2020
INVENTOR(S) : Chelsie Conrad et al.

It is certified that error appears in the above-identified patent and that said Letters Patent is hereby corrected as shown below:

In the Specification

Column 4, Line 40, "lid" should be --1/d--.

Signed and Sealed this
Nineteenth Day of July, 2022

Katherine Kelly Vidal
*Director of the United States Patent and Trademark Office*